United States Patent [19]

Tsunewaki et al.

[11] Patent Number: 4,680,888
[45] Date of Patent: Jul. 21, 1987

[54] HYBRID SEED PRODUCTION IN COMMON WHEAT USING CYTOPLASMIC MALE STERILITY

[75] Inventors: Koichiro Tsunewaki, Kyoto; Ichiro Ohtsuka, Hiratsuka, both of Japan

[73] Assignee: Sumitomo Chemical Company, Limited, Japan

[21] Appl. No.: 772,995

[22] Filed: Sep. 5, 1985

[30] Foreign Application Priority Data

Sep. 18, 1984 [JP] Japan .................. 59-195580

[51] Int. Cl.$^4$ .............................. A01H 1/02
[52] U.S. Cl. ...................... 47/58; 47/DIG. 1
[58] Field of Search ............ 47/58, DIG. 1; 800/1

[56] References Cited

U.S. PATENT DOCUMENTS 4,143,486  3/1979  Maan ......................... 47/58
4,351,130  9/1982  Rutger et al. .

OTHER PUBLICATIONS

Mukai, Y. et al., Proceedings of the 5th International Wheat Genetics Symposium, pp. 282–292 (1978).
Ogihara, Y. et al., Japanese Journal of Genetics 57, 371–396 (1982).
Sasakuma, T. et al., Seiken Ziho 27–28, 59–65 (1979).

Primary Examiner—Robert E. Bagwill
Attorney, Agent, or Firm—Darby & Darby

[57] ABSTRACT

Commercial hybrid wheat is produced by growing under a condition of, for example, not less than 14 hours day length (condition A) common wheat variety in which $D^2$-type cytoplasma from Aegilops species has been introduced until cytoplasmic male-sterility is induced, producing hybrid seeds by growing in alternating blocks with a pollinator parent with a good combining ability, maintaining the said male-sterile $D^2$-type alloplasmic lines by self pollination by growing under condition of, for example, less than 14 hours day length (condition B), and harvesting by growing the said hybrid under condition A or B.

5 Claims, 3 Drawing Figures

HYBRID SEED PRODUCTION IN COMMON WHEAT USING CYTOPLASMIC MALE STERILITY

This invention is concerned with commercial hybrid wheat production using conditional cytoplasmic male sterility.

Figure 1:
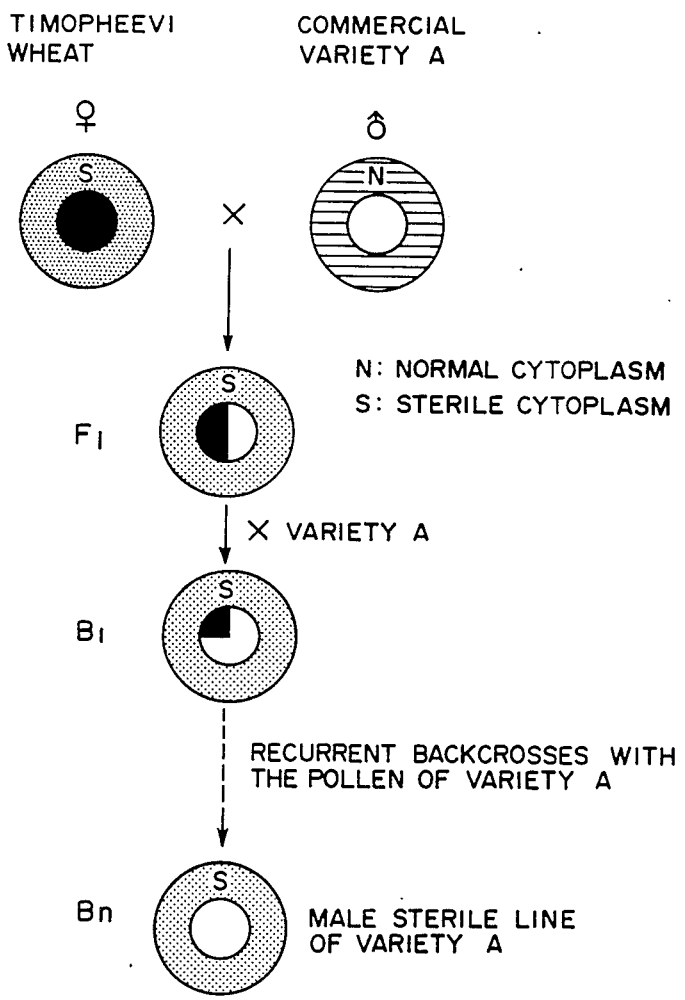
Figure 2:
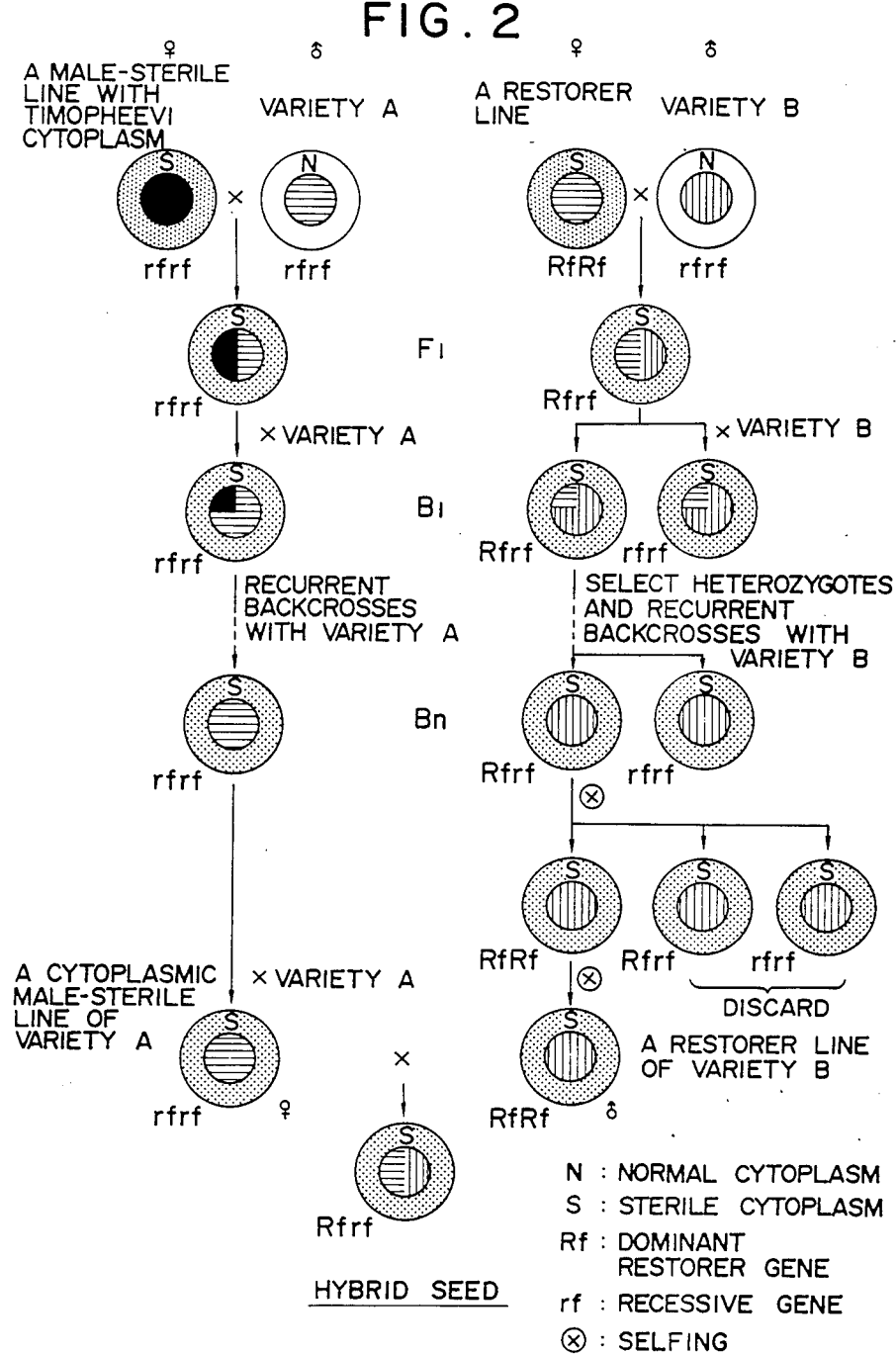

It is a well known fact that a cytoplasmic male sterile wheat line can be obtained by backcrossing a wild wheat or a species belonging to Aegilops or Secale with the pollen of a common wheat variety (FIG. 1). Cytoplasmic male sterility provides commercial utilization of $F_1$ hybrids, but this phenomenon in itself does not serve as a practical wheat improvement tool. For this purpose, a fertility-restoring line is needed to reestablish male fertility in the $F_1$ generation. Supposing that heterosis for productivity is expressed in the $F_1$ plants from a cross between varieties A and B, the male-sterile line of A (or B) and the restorer line of B (or A) should be developed for commercially available hybrid wheat production. As illustrated in FIG. 2, the former line can be produced by recurrent backcrosses of a wheat line having sterile cytoplasm with the pollen of variety A. The latter can be produced by backcrossing a line having a dominant restorer gene (Rf) with the pollen of variety B. In the latter case, male fertile plants having the Rf gene should be visually selected and crossed with variety B in every generation. After five backcrosses or more, the selfing will be made, and in the next generation the male-fertile homozygous plants should be selected. The progeny of these plants will be a restorer line of variety B. Thus, both lines will be grown in field side by side, and then the $F_1$ seeds set on the male-sterile line by natural cross pollination will be harvested and commercially available.

Since 1960s, many studies have been made in various universities and seed companies to develop hybrid wheat varieties. These studies have shown that a source of male sterile cytoplasms is very limited for hybrid seed production. The male-sterile cytoplasm from Timopheevi wheats (*Triticum timopheevi* Zhuk.) has been exclusively used for this purpose. However, this cytoplasm has been shown to have undesirable side effects on the $F_1$ plants, such as incomplete restoration of male fertility and seed shrivelling, which reduce productivity of the hybrid. Therefore, the lowered levels of heterosis have not compensated for increased seed costs projected by the complicated breeding programs described above, production costs and marketing. Such high costs of hybird seeds would not be acceptable to wheat producers.

Our system for hybrid seed production is substantially different from the above-mentioned system. Moreover, its advantage is that the breeding program is more simplified; and therefore, the hybrid seeds can be produced and marketed at much lower cost. This method will be described below.

Figure 3:
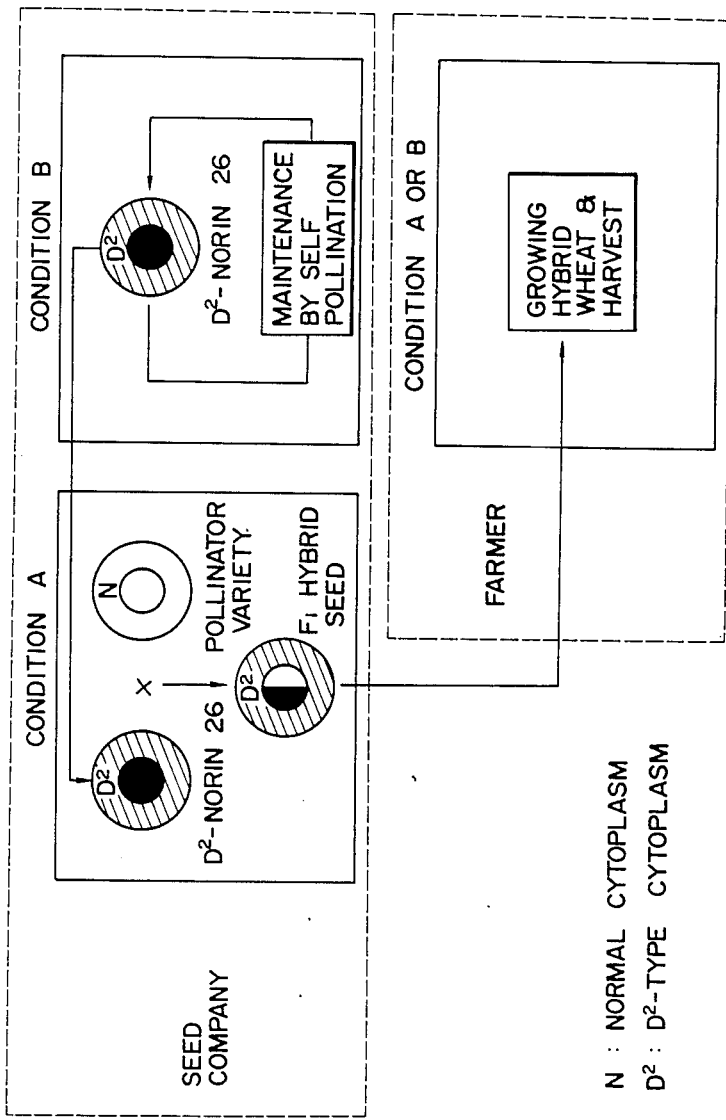

In the accompanying drawings,

FIG. 1 is procedure of developing a cytoplasmic male-sterile line of commercial wheat variety;

FIG. 2 is breeding program for hybrid seed production using the male-sterile cytoplasm from *Triticum timopheevi;* and FIG. 3 is a new system for hybrid seed production using conditional cytoplasmic male sterility expressed in the alloplasmic line of Norin 26 with the $D^2$-type cytoplasm (abbreviated, $D^2$-Norin 26). Condition A: a condition of not less than 14 hours day length, and condition B: a condition of less than 14 hours day length.

Mukai et al., Proc. 5th Intern. Wheat Genet. Symp. pp. 282-292 (1978) classified the cytoplasm from *Aegilops crassa* 4x and 6x, *Ae. juvenalis* or *Ae. vavilovii* as a plasma type $D^2$. This plasma type can be distinguished from other plasma types by comparing the restriction enzyme fragment patterns of chloroplast DNAs (Ogihara and Tsunewaki, Jpn. J. Genet. 57: 371-396 (1982)). As presented in Table 1, when digested with restriction enzymes BamHI, EcoRI, HindIII, KpnI, PstI, SmaI and XhoI, the chloroplast DNA of $D^2$-type cytoplasm differs from that of B-type cytoplasm (common wheat cytoplasm) by a total of fourteen fragments. The Aegilops species described above were recurrently backcrossed as female parents with the pollen of a Japanese variety, Norin 26, and the alloplasmic lines of Norin 26 with the $D^2$-type cytoplasm have been thus established. As presented in Table 2, the alloplasmic lines with *Ae. crassa* 4x and 6x, *Ae. juvenalis* and *Ae. vavilovii* are all male fertile (range: 63.1%-71.1% selfed seed set), when the plants were grown under field condition in Kyoto, Japan. However, we have found an intriguing fact when these alloplasmic lines were grown in an artficially illuminated green house under a condition of 17 hr light and 7 hr dark: The selfed seed sets of these alloplasmic lines were remarkably reduced, ranging from 0.8% to 6.2%, while the normal Norin 26 had 99.2% seed set. Sasakuma and Ohtsuka, Seiken Ziho 27-28:59-65 (1979), observed complete male sterility expressed in the plants of the $D^2$-type alloplasmic lines grown in the northern part of Japan, Hokkaido, because of another malformation and pistillody.

TABLE 1

The differences in the restriction enzyme fragment patterns of chloroplast DNAs between plasma type B (common wheat cytoplasm) and plasma type $D^2$.

| | Plasma type B | | Plasma type $D^2$ | | |
|---|---|---|---|---|---|
| Fragment code | No. of fragments | Molecular weight (kbp) | Fragment code | No. of fragments | Molecular weight (kbp) | Difference from type B (kbp) |
| B2 | 1 | 9.6 | B2l | 1 | 10.5 | +0.9 |
| B7 | 1 | 5.5 | B7l | 1 | 5.8 | +0.3 |
| B21 | 2 | 1.4 | B2l | 1 | 1.4 | −1.4 |
| E7 | 1 | 2.7 | E7l | 1 | 3.4 | +0.7 |
| H2 | 1 | 9.0 | H2l | 1 | 10.1 | +1.1 |
| H3 | 1 | 8.0 | H3s | 1 | 6.7 | −1.3 |
| H5 | 1 | 5.9 | H5l | 1 | 6.0 | +0.1 |
| H6 | 1 | 5.6 | H6l | 1 | 5.8 | +0.2 |
| K3 | 1 | 15.4 | K3l | 1 | 15.6 | +0.2 |
| P7 | 1 | 8.1 | P7l | 1 | 8.3 | +0.2 |

TABLE 1-continued

The differences in the restriction enzyme fragment patterns of chloroplast DNAs between plasma type B (common wheat cytoplasm) and plasma type $D^2$.

| Plasma type B | | | Plasma type $D^2$ | | | |
|---|---|---|---|---|---|---|
| Fragment code | No. of fragments | Molecular weight (kbp) | Fragment code | No. of fragments | Molecular weight (kbp) | Difference from type B (kbp) |
| Sm11 | 1 | 21.1 | Sm1 + Sm18 | 1 + 1 | 20.8 + 0.8 | +0.5 |
| Sm5 | 1 | 8.5 | Sm51 | 1 | 8.8 | +0.3 |
| Sm4b | 1 | 11.4 | Sm7 + Sm86 | 1 + 1 | 7.3 + 5.0 | +0.9 |
| X3 | 1 | 13.1 | X31 | 1 | 14.4 | +1.3 |

TABLE 2

Selfed seed fertility (%) of normal and alloplasmic lines of Norin 26

| Line | Cytoplasm donor | Field (Kyoto 1981) | Field (Kyoto 1982) | Greenhouse* (Kyoto 1983) |
|---|---|---|---|---|
| Norin 26 | — | 99.0 | 98.6 | 99.2 |
| $D^2$-Norin 26 | Aegilops crassa (4×) | 100.0 | 89.6 | 6.2 |
| " | Ae. crassa (6×) | 87.5 | 71.1 | 1.1 |
| " | Ae. juvenalis | 48.0 | 63.1 | 0.8 |
| " | Ae. vavilovii | 62.5 | 66.6 | 1.2 |

*In greenhouse, plants were grown under a condition of 17 hr light and 7 hr dark. (Note) $D^2$-Norin 26: an alloplasmic line of Norin 26 with the $D^2$-type cytoplasm.

We are the first to report that the male sterility is expressed only in the long-day environments. The photoperiodism is most critical factor for the conversion of the male-fertile character to complete male-sterile, and this phenomenon may be called "conditional" cytoplasmmic male sterility. The observation of Sasakuma and Ohtsuka (1979) can be interpreted as follows: In Hokkaido, the reproductive stage of wheat initiates from the middle of May, and the heading period is from mid to late June. The day length during the reproductive stage of wheat is more than 14 hours in this area, and wheat plants are obviously exposed to the long-day environments. Therefore, we conclude that, naturally or artificially, male sterility can be induced by the long-day treatment of the $D^2$-type alloplasmic lines having the Norin 26 genes.

Plasma type $D^2$ has not been considered as a source of male-sterile cytoplasm in order to develop hybrid wheat varieties. This is because most of the experiments have shown that various alloplasmic lines of wheat varieties, except Norin 26, with the $D^2$-type cytoplasm are completely male-fertile. However, our finding will lead to the possibility of the utilization of the $D^2$-type cytoplasm-inducing male sterility for hybrid seed production. We will describe a new production method of commercially available hybrid seeds as follows:

In this report, we define condition A as a condition under which male-sterility can be induced in common wheat varieties, such as a long-day condition, of not less than 14 hours light, which will be exposed to wheat plants during the reproductive stage. This condition can be achieved naturally be choosing cultivation regions and seasons (e.g., the area of higher latitude such as Hokkaido, Japan), and artificially by applying additional illumination to wheat plants. On the other hand, condition B is defined as a condition under which male fertility can be induced in common wheat, such as a natural or artificial environment of less than 14-hour day length during the reproductive stage As illustrated in FIG. 3, the production of commercial $F_1$ hybrid seeds will be conducted under condition A. Such hybrid seeds will be obtained through natural cross pollination by growing the male-sterile alloplasmic Norin 26 in alternating blocks with a pollinator parent under condition A.

The alloplasmic Norin 26 will be maintained by self pollination in the area under condition B. These seed operations will be conducted by seed companies, and the hybrid seeds thus produced will be processed and enter wheat seeds market. Farmers will grow hybrid wheat in seed production areas under condition A or B.

As already stated briefly, the obvious advantages of our system for hybrid seed production are as follows: (1) Hybrid wheat can be developed and produced at much lower cost. The conventional system using the T. timopheevi male-sterile cytoplasm (plasma type G) requires the development of fertility-restoring lines as pollinator parents in order to reestablish male fertility in the next generation. However, this procedure is most expensive and time-consuming. The use of conditional cytoplasmic male sterility does not necessitate the development and use of such fertility-restoring lines; instead, currently grown commercial varieties can be used as pollinator parents for hybrid seed production. (2) There is an essential difference in male-sterile maintenance between the conventional and the present systems. The maintenance of a male-sterile line with T. timopheevi cytoplasm should be accomplished by growing it together with its normal but nonrestoring counterpart. Seed will be harvested from the male-sterile line and used for further maintenance and hybrid seed production. In contrast, the $D^2$-type alloplasmic lines of Norin 26 in themselves are male fertile under condition B; and therefore, they can be maintained by self pollination. This means that our system is more efficient in seed increase of male-sterile lines than the conventional system, because the former leads to higher levels of seed set than the latter. At the same time, the contamination from unwanted varieties grown in the same area can be more reduced because of self pollination. In summary, male-sterile maintenance is more economical, and the genetic uniformity of male-sterile lines is more efficiently maintained in seed increase generations.

EXAMPLES

Using the alloplasmic lines with the $D^2$-type cytoplasm, hybrid performance was tested in two experiments, and the data are presented in Tables 3 and 4.

TABLE 3

Average performance of the nine agronomic characters in normal or alloplasmic Norin 26, Norin 61, and their reciprocal $F_1$ hybrids

| Line | Heading date | Plant height (cm) | No. of ears | Ear length (cm) | No. of spikelets | % Sterility (%) | Grain weight/ ear (g) | Grain weight/ plant (g) | No. of grains/ plant |
|---|---|---|---|---|---|---|---|---|---|
| Norin 26 | 8.6 | 82.3 | 7.7 | 8.1 | 18.6 | 2.0 | 1.4 | 10.4 | 319 |
| $D^2$-Norin 26 | 8.8 | 78.7 | 7.6 | 8.2 | 18.0 | 12.8 | 0.9 | 6.5 | 191 |
| Norin 61 | 9.5 | 79.6 | 7.0 | 8.9 | 18.0 | 1.4 | 1.4 | 9.6 | 301 |
| (Norin 26 × Norin 61)$F_1$ | 8.1 | 85.4 | 8.5 | 9.0 | 18.4 | 1.4 | 1.5 | 11.5 | 350 |
| (Norin 61 × Norin 26)$F_1$ | 7.2 | 86.7 | 9.9 | 9.3 | 18.3 | 0.9 | 1.5 | 15.9 | 481 |
| ($D^2$-Norin 26 × Norin 61)$F_1$ | 8.8 | 82.6 | 8.0 | 8.9 | 18.0 | 1.8 | 1.3 | 10.7 | 302 |
| (Norin 61 × $D^2$-Norin 26)$F_1$ | 8.0 | 87.5 | 9.0 | 9.0 | 18.3 | 1.7 | 1.7 | 15.1 | 440 |

TABLE 4

Average performance of the nine agronomic characters in normal or alloplasmic Chinese Spring, Norin 61, and their reciprocal $F_1$ hybrids

| Line | Heading date | Plant height (cm) | No. of ears | Ear length (cm) | No. of spikelets | % Sterility (%) | Grain weight/ ears (g) | Grain weight/ plant (g) | No. of grains/ plant |
|---|---|---|---|---|---|---|---|---|---|
| CS | 22.3 | 101.6 | 7.5 | 7.9 | 22.8 | 1.8 | 1.0 | 7.2 | 268 |
| $D^2$-CS | 24.1 | 104.8 | 8.0 | 7.7 | 22.4 | 1.8 | 0.8 | 6.4 | 252 |
| Norin 61 | 9.8 | 66.0 | 7.4 | 8.7 | 16.2 | 1.1 | 1.3 | 9.7 | 288 |
| (CS × Norin 61)$F_1$ | 13.4 | 88.0 | 8.4 | 9.1 | 20.0 | 5.7 | 1.3 | 11.2 | 370 |
| (Norin 61 × CS)$F_1$ | 13.1 | 92.4 | 8.8 | 9.2 | 20.6 | 1.5 | 1.5 | 13.6 | 422 |
| ($D^2$-CS × Norin 61)$F_1$ | 13.0 | 99.9 | 9.2 | 9.2 | 20.5 | 1.6 | 1.4 | 12.6 | 392 |
| (Norin 61 × $D^2$-CS)$F_1$ | 13.5 | 93.1 | 9.4 | 9.1 | 21.0 | 1.5 | 1.3 | 12.8 | 412 |

Both experiments consisted of four replications, in each of which four plants of $F_1$ hybrids and ten plants of their parental lines were transplanted and grown in an experimental field of Kyoto, Japan, at a rate of 30 cm between rows and 10 cm between plants. Data were taken from the plants in each replication on the following nine agronomic characters: (1) heading data (May 1=1), (2) plant height, (3) number of ears per plant, (4) ear length, (5) number of spikelets, (6) percent of sterility, (7) grain number per ear, (8) number of grain per plant, and (9) grain weight per plant. Table 3 shows the average performance of the eight characters in alloplasmic Norin 26 with the $D^2$-type cytoplasm (from *Ae. vavilovii*) or normal Norin 26, Norin 61, and their handmade reciprocal $F_1$ hybrids. In all the $F_1$ hybrids, heterosis was observed for agronomic characters such as number of ears and ear length. However, the $D^2$-Norin 26 × Norin 61 hybrid did not exceed their parents very much in grain weight and number per plant. This may be due to inefficient male-fertility restoration in the $F_1$ hybrid. As presented in Table 4, heterotic effects on grain weight and number per plant were found in the $F_1$ hybrid from a cross between the $D_2$-type alloplasmic Chinese Spring and Norin 61. These results suggest that the choice of an excellent combiner variety with alloplasmic Norin 26 would lead to profitably higher yield of the hybrid than commercial wheat varieties such as Norin 26. To date, male sterility is observed only in the alloplasmic lines of Norin 26 with the $D^2$-type cytoplasm. However, the male-sterility character could be transferred to other commercial wheat varieties, such as Norin 61 (*Triticum aestivum* L.), Takari (*Triticum aestivum* L.), Newton (*Triticum aestivum* L.) by backcrosses and selection, so that our system for hybrid seed production (FIG. 3) is not restricted only to the use of the alloplasmic Norin 26.

One of the important factors for the success of hybrid wheat is whether acceptable cross pollination is obtained in hybrid seed production fields or not. Table 5 presents the seed sets on male-sterile lines of Norin 26 with *T. timopheevi* cytoplasm naturally cross-pollinated with Japanese varieties Junrei-komugi, Nichirin-komugi and Norin 68.

TABLE 5

Seed set on the male-sterile line of Norin 26 with *T. timopheevi* cytoplasm by natural cross pollination

| Cross combination | | Seed set on male-sterile line | | | |
|---|---|---|---|---|---|
| Male-sterile line | Pollinator variety | Replication | No. of ears | % Seed set | No. of grains |
| Norin 26 | Junrei-komugi | 1 | 4.0 | 34.3 | 41.0 |
| | | 2 | 4.7 | 35.6 | 45.7 |
| | | 3 | 5.3 | 41.6 | 78.3 |
| | | Mean | 4.7 | 37.2 | 55.0 |
| Norin 26 | Nichirin-komugi | 1 | 4.7 | 31.7 | 60.7 |
| | | 2 | 4.7 | 25.6 | 48.7 |
| | | 3 | 4.7 | 25.3 | 48.3 |
| | | Mean | 4.7 | 27.5 | 52.6 |
| Norin 26 | Norin 68 | 1 | 7.0 | 23.7 | 59.0 |
| | | 2 | 4.7 | 18.5 | 32.7 |
| | | 3 | 4.5 | 12.6 | 27.0 |
| | | Mean | 5.4 | 18.3 | 39.6 |

The experiment was carried out with three replications in the experimental field of Kyoto, Japan. The male-sterile line was grown in its neighboring row with each of the pollinator parents (10 cm between plants and 30 cm between rows). Data on seed set were taken from three male-sterile plants in each replication, and the average value for each outcross was calculated. Although the weather condition in this growing season was not favorable for natural cross pollination, average outcrossing rates were 37.3%, 27.5% and 18.3%, respectively. Seed set on male-sterile varieties is also affected by the another characteristics varieties of pollinator varieties; therefore, if a wheat variety with high pollen-shedding ability, such as Norin 75, Junrei-komugi, Aoba-komugi is used as a pollinator, a seed set of at least 50% on male-sterile plants could be assured and might be economically acceptable.

We claim:

1. A method of commercial hybrid wheat production which comprises growing common wheat varieties to which $D^2$-type cytoplasm derived from Aegilops species has been introduced in a male-sterility inducing environment of not less than 14 hours daylight during the reproductive stage until male sterility is induced, producing hybrid seeds by growing in alternating blocks with a pollinator parent with a good combining ability, maintaining said male-sterile $D^2$-type alloplasmic lines by self pollination by growing said lines in a male fertility-inducing environment of less than 14-hour day length during the reproductive stage and harvesting after growing said hybrid.

2. The method according to claim 1 wherein the $D^2$-type cytoplasm is that of *Aegilops crassa* 4x and 6x, *Ae. juvenalis* or *Ae. vavilovii*.

3. The method according to claim 1 wherein the common wheat variety with the $D^2$-type cytoplasm is Norin 26.

4. The method of claim 1 wherein said growing step comprises growing said hybrid under said male-sterility inducing conditions.

5. The method of claim 1 wherein said growing step comprises growing said hybrid under said male-fertility inducing conditions.

* * * * *